United States Patent
Takaku et al.

(10) Patent No.: US 10,842,682 B2
(45) Date of Patent: Nov. 24, 2020

(54) NONWOVEN FABRIC LAYERED BODY, STRETCHABLE NONWOVEN FABRIC LAYERED BODY, FIBER PRODUCT, ABSORBENT ARTICLE, AND SANITARY MASK

(71) Applicant: MITSUI CHEMICALS, INC., Tokyo (JP)

(72) Inventors: Shouichi Takaku, Ichihara (JP); Kenichi Suzuki, Ichihara (JP); Tetsuya Yokoyama, Chonburi (TH); Koichi Shimada, Chiba (JP)

(73) Assignee: MITSUI CHEMICALS, INC., Tokyo (JP)

(*) Notice: Subject to any disclaimer, the term of this patent is extended or adjusted under 35 U.S.C. 154(b) by 0 days.

(21) Appl. No.: 15/556,501

(22) PCT Filed: Mar. 9, 2016

(86) PCT No.: PCT/JP2016/057462
§ 371 (c)(1),
(2) Date: Sep. 7, 2017

(87) PCT Pub. No.: WO2016/143834
PCT Pub. Date: Sep. 15, 2016

(65) Prior Publication Data
US 2018/0038025 A1  Feb. 8, 2018

(30) Foreign Application Priority Data

Mar. 9, 2015 (JP) .................................. 2015-046377

(51) Int. Cl.
*D04H 3/16* (2006.01)
*A41D 13/11* (2006.01)
(Continued)

(52) U.S. Cl.
CPC .............. *A61F 13/15* (2013.01); *A41D 13/11* (2013.01); *B32B 5/022* (2013.01); *B32B 5/26* (2013.01);
(Continued)

(58) Field of Classification Search
None
See application file for complete search history.

(56) References Cited

U.S. PATENT DOCUMENTS 5,470,639 A    11/1995  Gessner et al.
5,652,051 A *   7/1997  Shawver .................. D01F 6/30
                                                     442/362
(Continued)

FOREIGN PATENT DOCUMENTS

CN         1034010 A    7/1989
CN       103221600 A    7/2013
(Continued)

OTHER PUBLICATIONS

Espacenet translation of JP2002234976 (accessed on Oct. 12, 2018) (Year: 2002).*

(Continued)

*Primary Examiner* — Marla D McConnell
*Assistant Examiner* — Christine X Nisula
(74) *Attorney, Agent, or Firm* — Buchanan Ingersoll & Rooney PC (57) ABSTRACT

A nonwoven fabric layered body, including: an elastic nonwoven fabric; and an extensible spunbond nonwoven fabric that is disposed on at least one surface side of the elastic nonwoven fabric and that has a degree of maximum load elongation of 50% or more in at least one direction, the nonwoven fabric layered body satisfying the following (1) and (2). (1) The elastic nonwoven fabric includes a resin composition containing a specific low-crystalline polypro- (Continued)

pylene, and an α-olefin copolymer A containing an ethylene-derived constitutional unit and a propylene-derived constitutional unit, and having a melting point of 100° C. or more and a crystallization degree of 15% or less. (2) The resin composition contains from 5 parts by mass to 50 parts by mass of the α-olefin copolymer A with respect to 100 parts by mass of the resin composition.

15 Claims, 2 Drawing Sheets

(51) Int. Cl.
    *B32B 5/26*     (2006.01)
    *D04H 3/007*     (2012.01)
    *A61F 13/47*     (2006.01)
    *A61F 13/49*     (2006.01)
    *A61F 13/15*     (2006.01)
    *B32B 5/02*     (2006.01)

(52) U.S. Cl.
    CPC ............... *D04H 3/007* (2013.01); *D04H 3/16* (2013.01); *A61F 13/47* (2013.01); *A61F 13/49007* (2013.01); *B32B 2262/0253* (2013.01); *B32B 2307/726* (2013.01); *B32B 2555/02* (2013.01)

(56) References Cited

U.S. PATENT DOCUMENTS

| | | | |
|---|---|---|---|
| 6,679,869 B1* | 1/2004 | Schlinz | A61F 13/15699 604/385.22 |
| 2004/0067710 A1 | 4/2004 | Tsujiyama et al. | |
| 2005/0130544 A1 | 6/2005 | Cheng et al. | |
| 2005/0244638 A1* | 11/2005 | Chang | D04H 1/4382 428/364 |
| 2008/0014819 A1 | 1/2008 | Suzuki et al. | |
| 2008/0085977 A1* | 4/2008 | Okamoto | C08L 23/10 525/240 |
| 2008/0199673 A1 | 8/2008 | Allgeuer et al. | |
| 2009/0068912 A1* | 3/2009 | Boscolo | D04H 3/147 442/329 |
| 2010/0124864 A1* | 5/2010 | Dharmarajan | B32B 37/144 442/401 |
| 2010/0255255 A1 | 10/2010 | Kawakami et al. | |
| 2012/0322330 A1 | 12/2012 | Takebe et al. | |
| 2013/0070518 A1 | 3/2013 | Eigler et al. | |
| 2013/0239283 A1* | 9/2013 | Yokoyama | D01F 6/06 2/9 |
| 2014/0155854 A1 | 6/2014 | MacDonald et al. | |

FOREIGN PATENT DOCUMENTS

| | | |
|---|---|---|
| EP | 2 022 879 A1 | 2/2009 |
| JP | H-07-503502 A | 4/1995 |
| JP | 2001-140158 A | 5/2001 |
| JP | 2001-303421 A | 10/2001 |
| JP | 2002234976 A * | 8/2002 |
| JP | 2004-238775 A | 8/2004 |
| JP | 2005-089870 A | 4/2005 |
| JP | 2007-321292 A | 12/2007 |
| JP | 2008-213284 A | 9/2008 |
| JP | 2009-504933 A | 2/2009 |
| JP | 2009-062667 A | 3/2009 |
| JP | 2009-079341 A | 4/2009 |
| JP | 2012-012759 A | 1/2012 |
| WO | WO 2007/138733 A1 | 12/2007 |
| WO | WO 2009/063892 A1 | 5/2009 |
| WO | WO 2012/070518 A1 | 5/2012 |

OTHER PUBLICATIONS

International Search Report (PCT/ISA/210) dated May 24, 2016, by the Japanese Patent Office as the International Searching Authority for International Application No. PCT/JP2016/057461.
Written Opinion (PCT/ISA/237) dated May 24, 2016, by the Japanese Patent Office as the International Searching Authority for International Application No. PCT/JP2016/057461.
International Search Report (PCT/ISA/210) dated May 24, 2016, by the Japanese Patent Office as the International Searching Authority for International Application No. PCT/JP2016/057462.
Written Opinion (PCT/ISA/237) dated May 24, 2016, by the Japanese Patent Office as the International Searching Authority for International Application No. PCT/JP2016/057462.
The First Examination Report issued by the State Intellectual Property Office of People's Republic of China in corresponding Chinese Patent Application No. 201680014157.7 dated Feb. 19, 2019 (14 pages including partial English translation).
Office Action dated Jun. 1, 2020, by the Intellectual Property India in corresponding Indian Patent Application No. 201717035515 with an English Translation of the Office Action. (5 pages).

\* cited by examiner

NONWOVEN FABRIC LAYERED BODY, STRETCHABLE NONWOVEN FABRIC LAYERED BODY, FIBER PRODUCT, ABSORBENT ARTICLE, AND SANITARY MASK

TECHNICAL FIELD

The present invention relates to a nonwoven fabric layered body, a stretchable nonwoven fabric layered body, a fiber product, an absorbent article, and a sanitary mask.

BACKGROUND ART

In recent years, nonwoven fabrics are widely used in various applications because of their excellent breathability and flexibility. Therefore, nonwoven fabrics are required to have various characteristics depending on the application thereof, and improvement of those characteristics is demanded.

For example, nonwoven fabrics used for sanitary materials such as disposable diapers and sanitary napkins, backings for poultices, and the like are required to have water resistance and excellent moisture permeability. Further, they are also required to have stretchability, bulkiness, and wearability depending on the sites where they are used.

As a method of imparting stretchability to nonwoven fabrics, a method in which a thermoplastic elastomer is used as a raw material for a spunbond nonwoven fabric (see, e.g., Japanese National-Phase Publication (JP-A) No. H07-503502), a method in which low-crystalline polypropylene is used (see, e.g., Japanese Patent Application Laid-Open (JP-A) No. 2009-62667 and Japanese Patent Application Laid-Open (JP-A) No. 2009-79341), and the like have been proposed.

JP-A No. 2009-62667 or JP-A No. 2009-79341 suggests the addition of high-crystalline polypropylene or a release agent to low-crystalline polypropylene for the improvement of stickiness or the like of spunbond nonwoven fabrics. WO2012/070518 discloses a layered body of a nonwoven fabric comprising low-crystalline polypropylene and an extensible spunbond nonwoven fabric.

SUMMARY OF INVENTION

Technical Problem

In the method described in JP-A No. 2009-62667 or JP-A No. 2009-79341, it is necessary to increase the amount of the high-crystalline polypropylene or the release agent to be added to the low-crystalline polypropylene in order to prevent reduction of formability (adhesion of the nonwoven fabric to various rotary units in an apparatus in steps of embossing and the like or to other portions that are brought into contact with the nonwoven fabric) which occurs when producing a spunbond nonwoven fabric using low-crystalline polypropylene. As a result, the obtained spunbond nonwoven fabric tends to have an increase in residual strain, thereby having poor stretchability. In the method described in WO2012/070518, stretchability is maintained by layering low-crystalline polypropylene and an extensible spunbond nonwoven fabric. However, there is a strong demand to further improve stretchability. There is also an additional demand to realize favorable texture and improvement in wearability and roll blocking resistance.

Here, the term "roll blocking" refers to a phenomenon in which, when a nonwoven fabric layered body is stored in a rolled form for a long period of time, overlapping nonwoven fabric layered bodies adhere to each other due to storage environment temperature or pressure applied to the nonwoven fabric layered bodies, thereby causing the roll to be solidified. With regard to the nonwoven fabric layered body comprising low-crystalline polypropylene disclosed in WO2012/070518, improvement in blocking resistance during long-term storage at high temperatures is required.

In view of the above problems, an object of the invention is to provide a nonwoven fabric layered body excellent in formability upon production, stretchability, texture, wearability, and roll blocking resistance, and a stretchable nonwoven fabric layered body, a fiber product, an absorbent article, and a sanitary mask using the same.

Solution to Problem

Means for solving the above-described problems includes the following embodiments.

<1> A nonwoven fabric layered body, comprising:
an elastic nonwoven fabric; and
an extensible spunbond nonwoven fabric that is disposed on at least one surface side of the elastic nonwoven fabric and that has a degree of maximum load elongation of 50% or more in at least one direction,
the nonwoven fabric layered body satisfying the following (1) and (2):
(1) the elastic nonwoven fabric comprises a resin composition containing a low-crystalline polypropylene satisfying the following (a) to (f), and an α-olefin copolymer A containing an ethylene-derived constitutional unit and a propylene-derived constitutional unit, and having a melting point of 100° C. or more and a crystallization degree of 15% or less, and
(2) the resin composition contains from 5 parts by mass to 50 parts by mass of the α-olefin copolymer A with respect to 100 parts by mass of the resin composition:
(a) [mmmm]=20 to 60 mol %
(b) [rrrr]/(1-[mmmm])≤0.1
(c) [rmrm]>2.5 mol %
(d) [mm]×[rr]/[mr]$^2$≤2.0
(e) weight average molecular weight (Mw)=10,000 to 200,000
(f) molecular weight distribution (Mw/Mn)<4,
wherein, in (a) to (d), [mmmm] represents a meso pentad fraction, [rrrr] represents a racemic pentad fraction, [rmrm] represents a racemic meso racemic meso pentad fraction, and [mm], [rr] and [mr] each represent a triad fraction.

<2> The nonwoven fabric layered body according to <1>, wherein the resin composition contains from 95 parts by mass to 50 parts by mass of the low-crystalline polypropylene with respect to 100 parts by mass of the resin composition.

<3> The nonwoven fabric layered body according to <1> or <2>, wherein the α-olefin copolymer A has a tensile elastic modulus of 100 MPa or less.

<4> The nonwoven fabric layered body according to any one of <1> to <3>, wherein the α-olefin copolymer A is a copolymer comprising constitutional units derived from ethylene, propylene, and butene.

<5> The nonwoven fabric layered body according to any one of <1> to <4>, wherein the extensible spunbond nonwoven fabric is disposed on both surface sides of the elastic nonwoven fabric.

<6> The nonwoven fabric layered body according to any one of <1> to <5>, wherein the elastic nonwoven fabric is a nonwoven fabric obtained by a spunbond method.

<7> The nonwoven fabric layered body according to any one of <1> to <6>, wherein the extensible spunbond nonwoven fabric is an extensible spunbond nonwoven fabric comprising a concentric core-sheath-type composite fiber comprising, as a core portion, a low-MFR propylene-based polymer having an MFR in a range of from 1 g/10 minutes to 200 g/10 minutes and, as a sheath portion, a high-MFR propylene-based polymer having an MFR in a range of from 16 g/10 minutes to 215 g/10 minutes, and wherein a difference in MFR between the low-MFR propylene-based polymer and the high-MFR propylene-based polymer is 15 g/10 minutes or more.

<8> The nonwoven fabric layered body according to any one of <1> to <7>, wherein the extensible spunbond nonwoven fabric comprises an olefin-based polymer composition containing from 80% by mass to 99% by mass of a crystalline propylene-based polymer and from 1% by mass to 20% by mass of a high-density polyethylene.

<9> The nonwoven fabric layered body according to any one of <1> to <8>, wherein a weight-per-area ratio of the elastic nonwoven fabric and the extensible spunbond nonwoven fabric (elastic nonwoven fabric:extensible spunbond nonwoven fabric) is in a range of from 10:90 to 90:10.

<10> A stretchable nonwoven fabric layered body, obtained by drawing the nonwoven fabric layered body according to any one of <1> to <9>.

<11> A fiber product, comprising the nonwoven fabric layered body according to any one of <1> to <9> or the stretchable nonwoven fabric layered body according to <10>.

<12> An absorbent article, comprising the nonwoven fabric layered body according to any one of <1> to <9> or the stretchable nonwoven fabric layered body according to <10>.

<13> A sanitary mask, comprising the nonwoven fabric layered body according to any one of <1> to <9> or the stretchable nonwoven fabric layered body according to <10>.

Advantageous Effects of Invention

According to the invention, a nonwoven fabric layered body excellent in formability upon production, stretchability, texture, wearability, and roll blocking resistance, and a stretchable nonwoven fabric layered body, a fiber product, an absorbent article, and a sanitary mask using the same are provided.

DESCRIPTION OF EMBODIMENTS

Embodiments for carrying out the invention will be described in detail below. Note that the invention is not limited to the embodiments below. In the following embodiments, the constituent elements (also including element steps) are not essential except for a case in which they are specifically described to be essential or they are considered to be apparently essential in principle. The same applies to the numerical values and their ranges, which are not intended to limit the invention.

The term "steps" used herein includes not only separate steps but also steps that cannot be clearly distinguished from other steps as long as the objects of the steps are achieved.

Further, the numerical range shown herein by using "to" are indicative of the range including the respective minimum and maximum numerical values described before and after "to". The content of each component in a composition described herein, when the composition contains plural kinds of substances corresponding to the component, refers to the total amount of the plural kinds of substances, unless otherwise specified.

<Nonwoven Fabric Layered Body>

The nonwoven fabric layered body of the invention comprises:

an elastic nonwoven fabric; and an extensible spunbond nonwoven fabric that is disposed on at least one surface side of the elastic nonwoven fabric and that has a degree of maximum load elongation of 50% or more in at least one direction, the nonwoven fabric layered body satisfying the following (1) and (2):

(1) the elastic nonwoven fabric comprises a resin composition containing a low-crystalline polypropylene satisfying the following (a) to (f), and an α-olefin copolymer A containing an ethylene-derived constitutional unit and a propylene-derived constitutional unit, and having a melting point of 100° C. or more and a crystallization degree of 15% or less, and (2) the resin composition contains from 5 parts by mass to 50 parts by mass of the α-olefin copolymer A with respect to 100 parts by mass of the resin composition:

(a) [mmmm]=20 to 60 mol %
(b) [rrrr]/(1-[mmmm])≤0.1
(c) [rmrm]>2.5 mol %
(d) [mm]×[rr]/[mr]²≤2.0
(e) weight average molecular weight (Mw)=10,000 to 200,000
(f) molecular weight distribution (Mw/Mn)<4 wherein, in (a) to (d), [mmmm] represents a meso pentad fraction, [rrrr] represents a racemic pentad fraction, [rmrm] represents a racemic meso racemic meso pentad fraction, and [mm], [rr] and [mr] each represent a triad fraction.

The nonwoven fabric layered body of the invention has excellent formability and productivity because an extensible spunbond nonwoven fabric is disposed on at least one surface side of an elastic nonwoven fabric, thereby making it possible to prevent adhesion of a nonwoven fabric layered body to members such as various rotary units in an apparatus used in steps of embossing and the like. Further, as the spunbond nonwoven fabric is extensible, excellent stretchability of the elastic nonwoven fabric can be maintained. Furthermore, as the elastic nonwoven fabric comprises a specific resin composition, the nonwoven fabric layered body has a small residual strain and stretchability that has been improved compared with that of a conventional nonwoven fabric layered body. Moreover, texture, wearability, and roll blocking resistance are also favorable.

The nonwoven fabric layered body of the invention has preferably a structure in which at least an extensible spunbond nonwoven fabric is disposed on a surface at a side that is brought into contact with a rotary unit included in a nonwoven fabric manufacturing apparatus, and more preferably a structure in which an extensible spunbond nonwoven fabric is disposed on both surface sides of the elastic nonwoven fabric.

The nonwoven fabric layered body of the invention usually has a weight per area in a range of 360 g/m² or less, preferably 240 g/m² or less, more preferably 150 g/m² or less, and still more preferably from 120 g/m² to 15 g/m². The weight per area can be determined by the method used in the Examples described below.

The composition ratio of the elastic nonwoven fabric and the extensible spunbond nonwoven fabric can be determined depending on various applications, if appropriate. The ratio of the elastic nonwoven fabric:the extensible spunbond nonwoven fabric (weight-per-area ratio) is usually in a range of from 10:90 to 90:10, preferably from 20:80 to 80:20, and more preferably from 20:80 to 50:50. In a case in which there are two or more elastic nonwoven fabrics (or extensible spunbond nonwoven fabrics), the weight per area of the elastic nonwoven fabrics (or extensible spunbond nonwoven fabrics) is the sum of those of the two or more.

The nonwoven fabric layered body of the invention usually has a residual strain of 26% or less and preferably 25% or less in at least one direction. When the residual strain in at least one direction is 26% or less, stretchability is favorable. The residual strain can be determined by the method used in the Examples described below.

The nonwoven fabric layered body of the invention usually has a degree of maximum load elongation of 205% or more and preferably 230% or more in at least one direction. The degree of maximum load elongation can be determined by the method used in the Examples described below.

The nonwoven fabric layered body of the invention has a rate of remaining bosses of preferably 60% or more, more preferably 65% or more, and still more preferably 70% or more after drawing. When it has a rate of remaining bosses of 60% or more after drawing, it has favorable texture. The rate of remaining bosses can be determined by the method used in the Examples described below.

The nonwoven fabric layered body of the invention has a peel strength of preferably 10N or less, more preferably 9N or less, and still more preferably 8N or less after two overlapping sheets of the nonwoven fabric layered bodies are stored in an oven. When it has a peel strength of 10N or less, it has favorable roll blocking resistance. The peel strength can be determined by the method used in the Examples described below.

[Elastic Nonwoven Fabric]

The elastic nonwoven fabric included in the nonwoven fabric layered body of the invention comprises a resin composition containing a low-crystalline polypropylene satisfying (a) to (f) described below (hereinafter also simply referred to as a "low-crystalline polypropylene") and an α-olefin copolymer A containing an ethylene-derived constitutional unit and a propylene-derived constitutional unit and having a melting point of 100° C. or more and a crystallization degree of 15% or less.

According to the invention, the term "elastic nonwoven fabric" refers to a nonwoven fabric having a feature of recovering because of its elasticity when stress is released after drawing.

The elastic nonwoven fabric can be produced by various known methods. Specifically, examples of such method include a spunbond method, a melt-blown method, and a flash spinning method. Among elastic nonwoven fabrics, a spunbond nonwoven fabric obtained by a spunbond method or a melt-blown nonwoven fabric obtained by a melt-blown method is preferable.

The elastic nonwoven fabric usually has a weight per area in a range of 120 g/m² or less, preferably 80 g/m² or less, more preferably 50 g/m² or less, and still more preferably from 2 g/m² to 40 g/m².

A fiber as a component of the elastic nonwoven fabric usually has a fiber diameter of 50 μm or less, preferably 40 μm or less, and more preferably 30 μm or less.

(Resin Composition)

A resin composition as a component of the elastic nonwoven fabric contains from 5 parts by mass to 50 parts by mass of α-olefin copolymer A with respect to 100 parts by mass of the resin composition. The resin composition further contains preferably from 95 parts by mass to 50 parts by mass of low-crystalline polypropylene with respect to 100 parts by mass of the resin composition. A nonwoven fabric layered body containing an elastic nonwoven fabric comprising such resin composition has a small residual strain, excellent stretchability, a high degree of maximum load elongation, and excellent texture, wearability, and roll blocking resistance. The resin composition more preferably contains from 5 parts by mass to 45 parts by mass of α-olefin copolymer A and from 55 parts by mass to 95 parts by mass of low-crystalline polypropylene with respect to 100 parts by mass of the resin composition.

From the viewpoint of effectively achieving the object of the invention, the total content of α-olefin copolymer A and low-crystalline polypropylene in the total mass of the resin composition is preferably 80% by mass or more, more preferably 90% by mass or more, and still more preferably 95% by mass or more.

(α-Olefin Copolymer A)

α-olefin copolymer A contains an ethylene-derived constitutional unit and a propylene-derived constitutional unit, and has a melting point of 100° C. or more and a crystallization degree of 15% or less.

α-olefin copolymer A is not particularly limited as long as it satisfies the above-described conditions, and it may further contain one or more kinds of α-olefin-derived constitutional units other than ethylene or propylene. Examples of α-olefin other than ethylene or propylene include 1-butene, 1-hexene, 4-methyl-1-pentene, and 1-octene.

From the viewpoint of effectively achieving the object of the invention, the total proportion of an ethylene-derived constitutional unit and a propylene-derived constitutional unit in all the constitutional units of α-olefin copolymer A is preferably 80 mol % or more, more preferably 85 mol % or more, and still more preferably 90 mol % or more.

The melting point of α-olefin copolymer A is defined as the peak top of a peak observed on the highest temperature side of a melting endothermic curve that is obtained by retaining the copolymer A in a nitrogen atmosphere at −40° C. for 5 minutes and increasing the temperature at a rate of 10° C./minute using a differential scanning calorimeter (DSC). Specifically, it can be defined as the peak top of a peak observed on the highest temperature side of a melting endothermic curve that is obtained by retaining 5 mg of a sample in a nitrogen atmosphere at −40° C. for 5 minutes and increasing the temperature at a rate of 10° C./minute using a differential scanning calorimeter (manufactured by PerkinElmer Inc., DSC-7).

α-olefin copolymer A has a melting point of preferably 130° C. or more and more preferably 150° C. or more.

The crystallization degree of α-olefin copolymer A is calculated from a melting endothermic curve derived from melting of the major component selected from melting endothermic curves obtained by retaining the copolymer A in a nitrogen atmosphere at −40° C. for 5 minutes and increasing the temperature at a rate of 10° C./minute using a differential scanning calorimeter (DSC). Specifically, it can be calculated by the following equation based on a melting endothermic curve derived from melting of the major component selected from melting endothermic curves obtained by retaining 5 mg of a sample in a nitrogen atmosphere at −40° C. for 5 minutes and increasing the temperature at a rate of 10° C./minute using a differential scanning calorimeter (manufactured by PerkinElmer Inc., DSC-7).

Crystallization degree=$\Delta H/\Delta H0 \times 100$(%)

In the equation, $\Delta H$ represents a heat quantity upon melting (J/g), which is obtained from a melting endothermic curve derived from melting of the major component of α-olefin copolymer A comprising ethylene and propylene, and $\Delta H0$ represents a heat quantity upon melting (J/g) of a perfect crystal of the major component. In other words, in a case in which the major component is ethylene, $\Delta H0$ is 293 J/g, and in a case in which the major component is propylene, $\Delta H0$ is 210 J/g.

α-olefin copolymer A has a crystallization degree of preferably 10% or less and more preferably 8% or less.

α-olefin copolymer A has a tensile elastic modulus measured by a method in accordance with JIS K7161 (the edition of FY2011), which is preferably 100 MPa or less, more preferably 40 MPa or less, and still more preferably 25 MPa or less.

(Low-Crystalline Polypropylene)

Low-crystalline polypropylene is a polymer satisfying the following requirements (a) to (f).

(a) [mmmm]=20 to 60 mol %:

When the meso pentad fraction [mmmm] of low-crystalline polypropylene is 20 mol % or more, the occurrence of stickiness is suppressed, and when it is 60 mol % or less, the crystallization degree does not become excessively high, which results in favorable elastic recovery. The meso pentad fraction [mmmm] is preferably from 30 to 50 mol % and more preferably from 40 to 50 mol %.

The meso pentad fraction [mmmm] and the below-mentioned racemic pentad fraction [rrrr] and racemic meso racemic meso pentad fraction [rmrm] are determined in accordance with the method suggested by A. Zambelli et al. in "Macromolecules, 6, 925 (1973)", and the fractions are the meso fraction, racemic fraction, and racemic meso racemic meso fraction of a pentad unit in a polypropylene molecule chain measured based on signals of methyl groups in a $^{13}$C-NMR spectrum. When the meso pentad fraction [mmmm] increases, stereoregularity becomes high. In addition, the below-mentioned triad fractions [mm], [rr], and [mr] are also calculated by the method described above.

$^{13}$C-NMR spectrometry can be performed in compliance with the peak attribution proposed by A. Zambelli et al. in "Macromolecules, 8, 687 (1975)" using the apparatus under the conditions described below.

Apparatus: JNM-EX400 $^{13}$C-NMR apparatus manufactured by JEOL Ltd.
Method: Proton complete decoupling method
Concentration: 220 mg/ml
Solvent: Mixed solvent of 1,2,4-trichlorobenzene and heavy benzene at a ratio of 90:10 (volume ratio)
Temperature: 130° C.
Pulse width: 45°
Pulse repetition time: 4 seconds
Integration: 10000 times

[Calculation Formulae]

$M=m/S \times 100$ $R=\gamma/S \times 100$ $S=P\beta\beta+P\alpha\beta+P\alpha\gamma$ S: Signal intensity of side-chain methyl carbon atoms of all propylene units
Pββ: 19.8 to 22.5 ppm
Pαβ: 18.0 to 17.5 ppm
Pαγ: 17.5 to 17.1 ppm
γ: Racemic pentad chain: 20.7 to 20.3 ppm
m: Meso pentad chain: 21.7 to 22.5 ppm (b) [rrrr]/(1-[mmmm])≤0.1

The value of [rrrr]/[1-mmmm] is calculated from the pentad unit fraction described above, and it is an index of uniformity of the regularity distribution of low-crystalline polypropylene. When this value increases, a mixture of high-regularity polypropylene and atactic polypropylene is formed as in the case of conventional polypropylene that is produced using an existing catalyst system, which causes stickiness.

When low-crystalline polypropylene has a [rrrr]/(1-[mmmm]) value of 0.1 or less, stickiness of the obtained elastic nonwoven fabric is suppressed. In view of this, [rrrr]/(1-[mmmm]) is preferably 0.05 or less and more preferably 0.04 or less.

(c) [rmrm]>2.5 mol %

When the racemic meso racemic meso fraction [rmrm] of low-crystalline polypropylene exceeds 2.5 mol %, randomness of the low-crystalline polypropylene increases, resulting in further improvement of elastic recovery of the elastic nonwoven fabric. [rmrm] is preferably 2.6 mol % or more and more preferably 2.7 mol % or more. The upper limit thereof is usually about 10 mol %.

(d) [mm]×[rr]/[mr]$^2$≤2.0

[mm]×[rr]/[mr]$^2$ represents an index of randomness of low-crystalline polypropylene. When this value is 2.0 or less, the elastic nonwoven fabric has sufficient elastic recovery, and stickiness is also suppressed. As [mm]×[rr]/[mr]$^2$ becomes closer to 0.25, randomness increases. From the viewpoint of obtaining sufficient elastic recovery described above, [mm]×[rr]/[mr]$^2$ is preferably from more than 0.25 to 1.8 and more preferably from 0.5 to 1.5.

(e) Weight average molecular weight (Mw)=10,000 to 200,000

When low-crystalline polypropylene has a weight average molecular weight of 10,000 or more, viscosity of the low-crystalline polypropylene is at an appropriate level, which is not excessively low, thereby suppressing yarn breakage upon manufacturing of the elastic nonwoven fabric. In addition, when the weight average molecular weight is 200,000 or less, viscosity of the low-crystalline polypropylene does not become excessively high, resulting in improvement of spinnability. The weight average molecular weight is preferably from 30,000 to 150,000 and more preferably from 50,000 to 150,000. The method of measuring the weight average molecular weight will be described below.

(f) Molecular weight distribution (Mw/Mn)<4

When low-crystalline polypropylene has a molecular weight distribution (Mw/Mn) of less than 4, the occurrence of stickiness of the elastic nonwoven fabric is suppressed. The molecular weight distribution is preferably 3 or less.

The weight average molecular weight (Mw) is a weight average molecular weight in terms of polystyrene measured by the gel permeation chromatography (GPC) method using the apparatus under the conditions described below. The molecular weight distribution (Mw/Mn) is a value calculated from the number average molecular weight (Mn) and the weight average molecular weight (Mw) measured in the same manner.

[GPC Measuring Device]
Column: TOSO GMHHR-H (S) HT
Detector: RI detector WATERS 150 C for liquid chromatogram
[Measurement Conditions]
Solvent: 1,2,4-trichlorobenzene
Measurement temperature: 145° C.
Flow rate: 1.0 mL/minute
Sample concentration: 2.2 mg/mL
Injection volume: 160 μl
Calibration curve: Universal Calibration
Analysis program: HT-GPC (Ver. 1.0)

It is preferable for low-crystalline polypropylene to further satisfy the following (g). (g) The melting point (Tm-D) defined as the peak top of a peak observed on the highest temperature side of a melting endothermic curve obtained by retaining the polypropylene in a nitrogen atmosphere at −10° C. for 5 minutes and increasing the temperature at a rate of 10° C./minute using a differential scanning calorimeter (DSC) is 0° C. to 120° C.

When low-crystalline polypropylene has a melting point (Tm-D) of 0° C. or more, the occurrence of stickiness of the elastic nonwoven fabric is suppressed, and when it is 120° C. or less, sufficient elastic recovery can be achieved. In view of this, the melting point (Tm-D) is more preferably from 0° C. to 100° C., and still more preferably from 30° C. to 100° C.

The melting point (Tm-D) described above can be defined as the peak top of a peak observed on the highest temperature side of a melting endothermic curve obtained by retaining 10 mg of sample in a nitrogen atmosphere at −10° C. for 5 minutes and increasing the temperature at a rate of 10° C./minute using a differential scanning calorimeter (manufactured by PerkinElmer Inc., DSC-7).

Low-crystalline polypropylene can be synthesized using a homogeneous catalyst referred to as "metallocene catalyst" described in, for example, WO2003/087172.

The resin composition, α-olefin copolymer A, and low-crystalline polypropylene may contain, as optional components, various known additives such as an antioxidant, a heat stabilizer, a weathering stabilizer, an antistatic agent, a slip agent, an antifog agent, a lubricant, a dye, a pigment, a natural oil, a synthetic oil, and a wax within a range that does not impair the object of the invention.

[Extensible Spunbond Nonwoven Fabric]

An extensible spunbond nonwoven fabric as a component of the nonwoven fabric layered body of the invention is a nonwoven fabric that has a degree of maximum load elongation in at least one direction of 50% or more, preferably 70% or more, and more preferably 100% or more, and still more preferably exhibits substantially no elastic recovery.

The extensible spunbond nonwoven fabric has a weight per area in a range of usually 120 g/m² or less, preferably 80 g/m² or less, more preferably 50 g/m² or less, and still more preferably from 40 g/m² to 5 g/m².

A fiber as a component of the extensible spunbond nonwoven fabric has a fiber diameter of usually 50 μm or less, preferably 40 μm or less, and more preferably 30 μm or less.

An example of the extensible spunbond nonwoven fabric is a nonwoven fabric that is obtained by using one kind or two or more kinds of olefin-based polymers described below.

Examples of a nonwoven fabric that is obtained using olefin-based polymers include: (1) a spunbond nonwoven fabric made of a core-sheath-type composite fiber, a parallel-type composite fiber (side-by-side type composite fiber), or a crimped composite fiber comprising two or more kinds of olefin-based polymers having a difference in the flow-induced crystallization induction period of 100 seconds or more (a propylene-based polymer having a high melting point and a propylene-based polymer having a low melting point); (2) a spunbond nonwoven fabric made of a core-sheath-type composite fiber, a parallel-type composite fiber, or a crimped composite fiber comprising a propylene-based polymer and an ethylene-based polymer; and (3) a spunbond nonwoven fabric made of a concentric core sheath composite fiber comprising, as a core portion, a low-MFR propylene-based polymer having a melt flow rate (hereinafter also referred to as "MFR", ASTMD-1238, 230° C., 2160 g load) in a range of from 1 g/10 minutes to 1000 g/10 minutes and, as a sheath portion, a high-MFR propylene-based polymer having an MFR in a range of from 1 g/10 minutes to 1000 g/10 minutes, the polymers having an MFR difference of 1 g/10 minutes or more, preferably 15 g/10 minutes or more, more preferably 30 g/10 minutes or more, and still more preferably 40 g/10 minutes or more.

Specific examples include: (1) a spunbond nonwoven fabric obtained using an olefin-based polymer composition comprising 80% by mass to 99% by mass of a propylene homopolymer and 20% by mass to 1% by mass of high-density polyethylene; (2) a spunbond nonwoven fabric made of a core-sheath-type composite fiber, a parallel-type composite fiber, or a crimped composite fiber comprising a high-melting-point propylene-based polymer (preferably propylene homopolymer) having a melting point in a range of from 157° C. to 165° C. and a low-melting-point propylene.α-olefin random copolymer having a melting point in a range of from 130° C. to 150° C., which have the same or different MFR; and (3) a spunbond nonwoven fabric made of a concentric core-sheath-type composite fiber comprising, as a core portion, a low-MFR propylene-based polymer (preferably propylene homopolymer) having an MFR in a range of from 1 g/10 minutes to 200 g/10 minutes and, as a sheath portion, a high-MFR propylene-based polymer (preferably propylene homopolymer) having an MFR in a range of from 16 g/10 minutes to 215 g/10 minutes, the polymers having an MFR difference of 15 g/10 minutes or more.

A preferable example of the extensible spunbond nonwoven fabric is: (1) a spunbond nonwoven fabric made of a concentric core-sheath-type composite fiber comprising, as a core portion, a low-MFR high-melting-point propylene-based polymer (preferably propylene homopolymer) having an MFR in a range of from 10 g/10 minutes to 200 g/10 minutes and a melting point in a range of from 157° C. to 165° C. and, as a sheath portion, a high-MFR low-melting-point propylene.α-olefin random copolymer having an MFR in a range of from 10 g/10 minutes to 200 g/10 minutes and a melting point in a range of from 130° C. to 150° C., the polymers having an MFR difference of 1 g/10 minutes or more, a parallel-type composite fiber, or a crimped composite fiber; or (2) a spunbond nonwoven fabric made of a concentric core-sheath-type composite fiber comprising, as a core portion, a low-MFR propylene-based polymer (preferably propylene homopolymer) having an MFR in a range of from 1 g/10 minutes to 200 g/10 minutes and, as a sheath portion, a high-MFR propylene-based polymer (preferably propylene homopolymer) having an MFR in a range of from 31 g/10 minutes to 230 g/10 minutes, the polymers having an MFR difference of 30 g/10 minutes or more. These extensible spunbond nonwoven fabrics have particularly excellent extensibility when they have a degree of maximum load elongation in at least one direction of 110% or more.

(Olefin-Based Polymer)

In a case in which the extensible spunbond nonwoven fabric is formed from one kind or two or more kinds of olefin-based polymers, examples of olefin-based polymers include ethylene-based polymers, propylene-based polymers, and crystalline polymers that are homopolymers or copolymers of α-olefins such as ethylene, propylene, 1-butene, 1-hexene, 4-methyl-1-pentene, and 1-octene.

Specific examples of ethylene-based polymers include ethylene homopolymers such as high-pressure low-density polyethylene, linear low-density polyethylene (i.e., LLDPE), and high-density polyethylene (i.e., HDPE), and ethylene.α-olefin random copolymers.

Specific examples of propylene-based polymers include polypropylene (propylene homopolymer), and propylene.α-olefin random copolymers such as a propylene.1-butene random copolymer, a propylene.ethylene random copolymer, and a propylene.ethylene.1-butene random copolymer.

Specific examples of crystalline polymers include poly-1-butene and poly-4-methyl-1-pentene.

(Propylene-Based Polymer)

The propylene-based polymer described above is usually a crystalline resin that is manufactured and sold under the name of polypropylene. Specific examples include: a propylene homopolymer or a copolymer comprising, as the major component, propylene and, as a copolymerization component, one kind or two or more kinds of α-olefins having 2 or more carbon atoms (except 3 carbon atoms) and preferably 2 to 8 carbon atoms (except 3 carbon atoms) such as ethylene, 1-butene, 1-pentene, 1-hexene, 1-octene, and 4-methyl-1-pentene, which usually has a melting point (Tm) in a range of 155° C. or more and preferably from 157° C. to 165° C.; and a copolymer of propylene and one or two or more kinds of α-olefins having 2 or more carbon atoms (except 3 carbon atoms) and preferably 2 to 8 carbon atoms (except 3 carbon atoms) such as ethylene, 1-butene, 1-pentene, 1-hexene, 1-octene, and 4-methyl-1-pentene, which usually has a melting point (Tm) in a range of from 130° C. to less than 155° C. and preferably from 130° C. to 150° C. Examples of copolymers include random copolymers and block copolymers.

The melt flow rate (MFR: ASTM D-1238, 230° C., 2160 g load) of the propylene-based polymer is not particularly limited as long as the polymer can be melt-spun. The melt flow rate is usually in a range of from 1 to 1000 g/10 minutes, preferably from 5 to 500 g/10 minutes, and more preferably from 10 to 100 g/10 minutes.

(Olefin-Based Polymer Composition)

It is preferable for the extensible spunbond nonwoven fabric according to the invention to be formed from an olefin-based polymer composition comprising an ethylene-based polymer and a propylene-based polymer. The olefin-based polymer composition usually includes the propylene-based polymer in a range of from 80% to 99% by mass and preferably 84% to 96% by mass, and the ethylene-based polymer in a range of from 1% to 20% by mass and preferably 4% to 16% by mass (wherein the propylene-based polymer+the ethylene-based polymer=100% by mass).

The ethylene-based polymer contained in the olefin-based polymer composition is not particularly limited; however, it is preferably a high-density polyethylene having a density in a range of from 0.94 to 0.97 g/cm$^3$, more preferably from 0.95 to 0.97 g/cm$^3$, and still more preferably from 0.96 to 0.97 g/cm$^3$. In addition, the melt flow rate (MFR: ASTM D 1238, 190° C., 2160 g load) of the ethylene-based polymer is not particularly limited as long as the polymer has spinnability. From the viewpoint of exhibition of extensibility, the melt flow rate is usually in a range of from 0.1 to 100 g/10 minutes, more preferably 0.5 to 50 g/10 minutes, and still more preferably 1 to 30 g/10 minutes.

The olefin-based polymer, ethylene-based polymer, and propylene-based polymer described above may contain, as optional components, various publicly known additives such as an antioxidant, a heat stabilizer, a weathering stabilizer, an antistatic agent, a slip agent, an antifog agent, a lubricant, a dye, a pigment, a natural oil, a synthetic oil, a wax, and a hydrophilic agent within a range that does not impair the object of the invention.

[Other Layers]

The nonwoven fabric layered body of the invention may have one layer or two or more layers other than layers of the elastic nonwoven fabric and the extensible spunbond nonwoven fabric depending on applications.

Specific examples of other layers include knitted fabrics, woven fabrics, nonwoven fabrics other than elastic nonwoven fabrics and extensible spunbond nonwoven fabrics, and films. A method of further layering (bonding) other layers on the nonwoven fabric layered body of the invention is not particularly limited. A variety of methods, including thermal fusion bonding methods such as hot embossing and ultrasonic fusion bonding, mechanical entangling methods such as needle punching and water jetting, methods using adhesives such as hot melt adhesives and urethane adhesives, and extrusion lamination, can be employed.

In a case in which the nonwoven fabric layered body of the invention has a nonwoven fabric other than the elastic nonwoven fabric and the extensible spunbond nonwoven fabric, examples of such nonwoven fabric include various known nonwoven fabrics such as spunbond nonwoven fabrics, meltblown nonwoven fabrics, wet nonwoven fabrics, dry nonwoven fabrics, dry pulp nonwoven fabrics, flash-spun nonwoven fabrics, and split-fiber nonwoven fabrics. These nonwoven fabrics may be stretchable or non-stretchable nonwoven fabrics. Here, the term "non-stretchable nonwoven fabrics" refers to nonwoven fabrics which do not produce recovery stress after elongation in MD (machine direction or longitudinal direction of nonwoven fabric) or CD (cross direction or direction perpendicular to the machine direction of nonwoven fabric).

In a case in which the nonwoven fabric layered body of the invention has a film, a breathable (moisture permeable) film is preferable in order to maintain breathability and hydrophilicity that are characteristics of the nonwoven fabric layered body of the invention. Examples of such breathable film include various known breathable films such as films of moisture permeable thermoplastic elastomers such as polyurethane elastomers, polyester elastomers, and polyamide elastomers, and porous films obtained by drawing thermoplastic resin films containing inorganic or organic fine particles to create pores in the films. Preferable thermoplastic resins used for the porous films are polyolefins such as high-pressure low-density polyethylene, linear low-density polyethylene (i.e., LLDPE), high-density polyethylene, polypropylene, a polypropylene random copolymer, and any combination thereof. Note that in a case in which it is not necessary to maintain breathability and hydrophilicity of the nonwoven fabric layered body, thermoplastic resin films of, for example, polyethylene, polypropylene, and any combination thereof may be used.

[Method for Producing Nonwoven Fabric Layered Body]

The nonwoven fabric layered body of the invention can be produced by a known method of producing a nonwoven fabric using a low-crystalline polypropylene and α-olefin copolymer A that are used as raw materials for the elastic nonwoven fabric, an olefin-based polymer that is used as a raw material for the extensible spunbond nonwoven fabric, and additives to be used if necessary.

As an example of the method of producing a nonwoven fabric layered body, a method using a nonwoven fabric manufacturing apparatus equipped with at least two lines of spinning units is described below.

At first, an olefin-based polymer, or two or more kinds of olefin-based polymers, if necessary, are molten in an extruder, or two or more extruders, if necessary, provided at the first-line spinning unit, and are introduced to a spinneret (die) fitted with a large number of spinning orifices (nozzles) or sheath-core spinning orifices, if necessary, and ejected. Thereafter, the continuous fibers comprising an olefin-based polymer that have been melt spun are introduced into a cooling chamber and cooled with cooling air. Then, the continuous fibers are drawn (towed) with drawing air and the extensible spunbond nonwoven fabric is deposited on the mobile collecting face.

Meanwhile, a resin composition comprising low-crystalline polypropylene and α-olefin copolymer A is molten in an extruder provided at the second-line spinning unit, and is introduced to a spinneret (die) fitted with a large number of spinning orifices (nozzles), and the resin composition is ejected. Thereafter, the continuous fibers comprising a resin composition that have been melt spun are introduced into a cooling chamber and cooled with cooling air. Then, the continuous fibers are drawn (towed) with drawing air and the resultant is deposited on the extensible spunbond nonwoven fabric, thereby forming an elastic nonwoven fabric.

The extensible spunbond nonwoven fabric may be deposited on the elastic nonwoven fabric using the third-line spinning unit, if necessary.

The temperature for melting the polymers that are used as raw materials for the elastic nonwoven fabric and the extensible spunbond nonwoven fabric is not particularly limited as long as the temperature is equal to or higher than the softening temperature or the melting point and is less than the thermal decomposition temperature of each polymer. The die temperature may vary depending on the polymers used. For example, the die temperature may be set to usually from 180° C. to 240° C., preferably from 190° C. to 230° C., and more preferably from 200° C. to 225° C. in the case of using a propylene-based polymer.

The temperature of the cooling air is not particularly limited as long as the polymer can be solidified. However, it is usually in a range of from 5° C. to 50° C., preferably 10° C. to 40° C., and more preferably 15° C. to 30° C. The speed of the drawing air is usually in a range of from 100 to 10,000 m/minute and preferably 500 to 10,000 m/minute.

It is preferable for the nonwoven fabric layered body of the invention to have a structure in which at least one part of the elastic nonwoven fabric and at least one part of the extensible spunbond nonwoven fabric are thermal-fusion-bonded. At such time, at least one part of the elastic nonwoven fabric and at least one part of the extensible spunbond nonwoven fabric may be pressed together using a nip roll before thermal fusion bonding.

A method of thermal fusion bonding is not particularly limited and it can be selected from various known methods. Exemplary prebonding methods include ultrasonic methods, hot embossing with embossing rolls, and hot air through methods. Of these, hot embossing is preferable because continuous fibers can be drawn efficiently upon drawing. The temperature range for hot embossing is preferably from 60° C. to 115° C.

In the case where the layered body is partially thermal-fusion-bonded by hot embossing, the embossing area rate is usually in a range of from 5% to 30% and preferably from 5% to 20%, and the non-embossing unit area is 0.5 mm² or more and preferably in a range of from 4 to 40 mm². The non-embossing unit area is the maximum area of a tetragon inscribed in bosses in the minimum unit of non-embossed portion surrounded by embossed portions. Examples of the embossing shapes include circles, ellipses, ovals, squares, rhomboids, rectangles, tetragons and continuations of shapes based on these shapes.

<Stretchable Nonwoven Fabric Layered Body>

The stretchable nonwoven fabric layered body of the invention is a nonwoven fabric layered body having stretchability, which is obtained by drawing the nonwoven fabric layered body described above.

The stretchable nonwoven fabric layered body of the invention can be obtained by drawing the nonwoven fabric layered body described above. A method of drawing is not particularly limited, and a conventionally known method can be used. In the method of drawing, partial drawing or overall drawing may be conducted. In addition, the method may involve monoaxial drawing or biaxial drawing. An example of a method of drawing in the machine direction (MD) is a method wherein a partially fusion-bonded mixed fiber is allowed to pass through two or more pairs of nip rolls. In this process, the partially fusion-bonded nonwoven fabric layered body may be drawn by operating the nip rolls at increasing rotational speeds along the machine direction. Alternatively, gear drawing may be performed using a gear drawing apparatus depicted in FIG. 1.

The drawing rate is preferably 50% or more, more preferably 100% or more, and still more preferably 200% or more, and it is preferably 1000% or less, and more preferably 400% or less.

The above drawing rate is preferably satisfied in the machine direction (MD) or the cross direction (CD) in the case of monoaxial drawing. In the case of biaxial drawing, the above drawing rate is preferably satisfied in at least one of the machine direction (MD) or the cross direction (CD).

Upon drawing at the above drawing rate, all the (continuous) fibers forming the elastic nonwoven fabric and the extensible spunbond nonwoven fabric are drawn. The continuous fibers forming the extensible spunbond nonwoven fabric layer(s) are plastically deformed to become extended (longer) in accordance with the drawing rate.

Thus, when the stress is released after the nonwoven fabric layered body is drawn, the (continuous) fibers forming the elastic nonwoven fabric undergo elastic recovery while the continuous fibers forming the extensible spunbond nonwoven fabric are folded without undergoing elastic recovery. As a result, the nonwoven fabric layered body exhibit bulkiness. Further, the continuous fibers forming the extensible spunbond nonwoven fabric become thinner, thereby improving softness and texture and imparting a function as an extension stopper.

<Fiber Product>

The fiber product of the invention comprises the nonwoven fabric layered body or stretchable nonwoven fabric layered body of the invention. Examples of the fiber product include, but are not particularly limited to, absorbent articles such as disposable diapers and sanitary napkins, hygiene materials such as sanitary masks, and medical articles such as bandages, clothing materials, and packaging materials. It is preferable for the fiber product of the invention to include, as a stretchy member, the nonwoven fabric layered body or stretchable nonwoven fabric layered body of the invention.

EXAMPLES

The invention will be described in greater detail based on the Examples hereinbelow without limiting the scope of the invention to such examples. Physical property values and the like were determined by the methods described below in the Examples and Comparative Examples.

(1) Weight Per Area [g/m²]

Six sheets of test pieces each having a length of 200 mm in the machine direction (MD) and a length of 50 mm in the cross direction (CD) were collected from a nonwoven fabric layered body. The sites of collection were randomly determined 3 sites in each of MD and CD (6 sites in total). Subsequently, the mass (g) of each collected test piece was measured using a top pan electronic balance (manufactured by Kensei Co., Ltd.). The mean value of mass of each test piece was calculated. The calculated mean value was converted to mass (g) per 1 m², and rounded to the nearest whole number to obtain the weight per area [g/m²].

(2) Maximum Load [N/50 mm] and Degree of Maximum Load Elongation [%]

Five sheets of test pieces each having a length of 200 mm in the machine direction (MD) and a length of 50 mm in the cross direction (CD) were collected from a nonwoven fabric layered body. Tensile test was conducted for the test pieces using a constant-rate extension type tensile tester at a chuck interval of 100 mm and a tensile speed of 100 mm/minute. The maximum load [N/50 mm] applied to each test piece was measured. In addition, the extension rate [%] of each test piece at the maximum load was determined. The mean value of five test pieces was calculated so that the maximum load and the degree of maximum load elongation were determined. The degree of maximum load elongation [%] of an extensible spunbond nonwoven fabric was determined by measurement according to the same method as described above.

(3) Residual Strain [%]

Five sheets of test pieces each having a length of 200 mm in the machine direction (MD) and a length of 50 mm in the cross direction (CD) were collected from a nonwoven fabric layered body. Each test piece was drawn using a constant-rate extension type tensile tester at a chuck interval of 100 mm, a tensile speed of 100 mm/minute, and a drawing rate of 100%, and then, the length of each test piece was immediately allowed to recover to the original length at the same speed. Further, each test piece was immediately drawn at the same speed and a drawing rate of 100%. Then, the length of each test piece was immediately allowed to recover to the original length at the same speed, and the strain upon recovery was determined. The mean value of five sheets of the nonwoven fabric layered bodies was evaluated as the residual strain (unit: %).

(4) Spinnability

The spinning state in the vicinity of the nozzle face of a spunbond nonwoven fabric manufacturing apparatus was visually observed and the number of times of yarn breakage per 5 minutes (unit: number of times/5 minutes) was counted. When the number of times of yarn breakage was 0 times/5 minutes, it was evaluated as "A". When yarn breakage occurred and it resulted in a failure of nonwoven fabric collection, it was evaluated as "C".

(5) Formability

A metal roll was operated for 5 minutes in the embossing step so that a state of adhesion occurring during passage of the nonwoven fabric layered body through a pair of embossing rolls was evaluated.

A: State in which no adhesion is visually confirmed.
B: State in which substantially no adhesion is visually confirmed.
C: State in which adhesion is visually confirmed or the nonwoven fabric layered body is wound around the embossing roll.

(6) Texture

Figure 1:
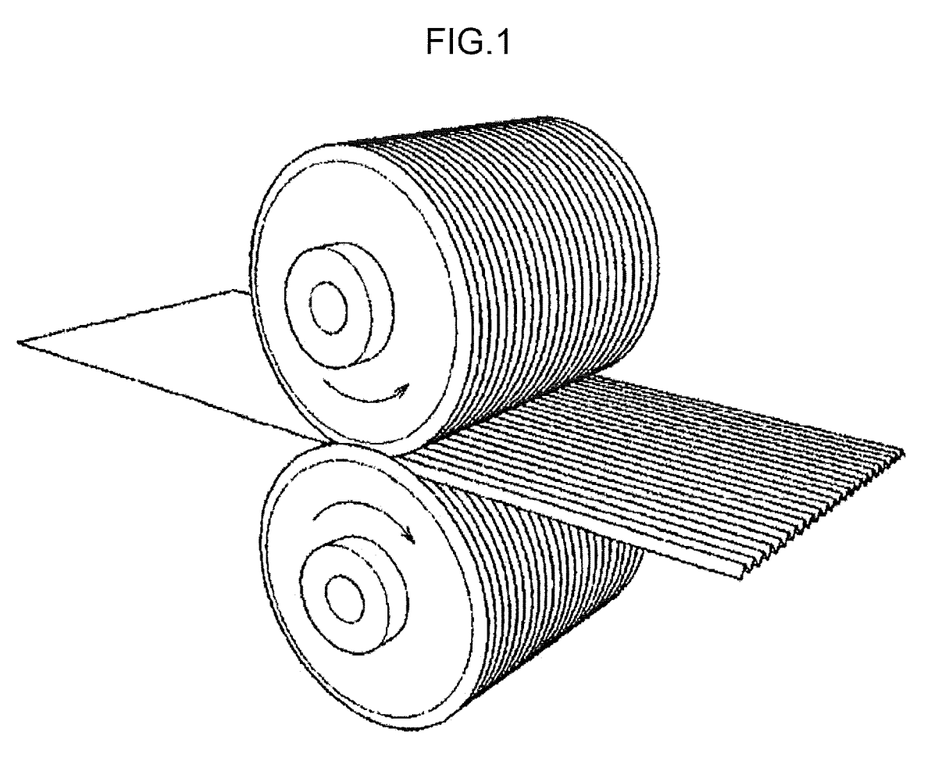
FIG. 1 schematically depicts a gear drawing apparatus.
Figure 2:
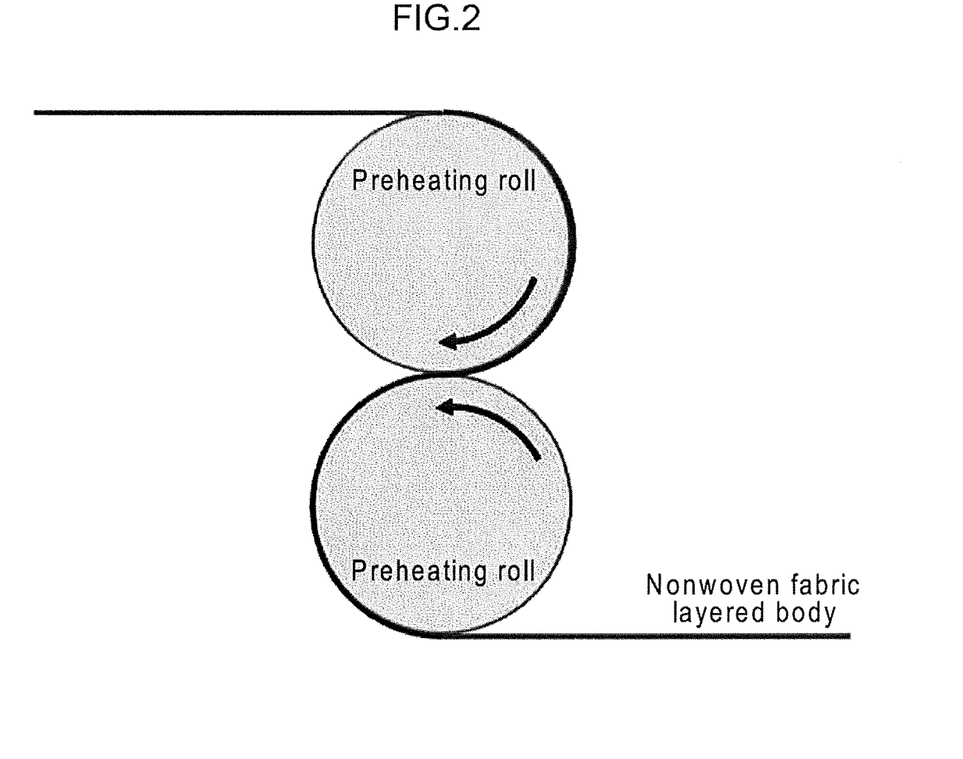
FIG. 2 schematically depicts a preheating apparatus.

One sheet of a test piece having a length of 250 mm in the machine direction (MD) and a length of 200 mm in the cross direction (CD) was collected from a nonwoven fabric layered body. The test piece was inserted in a manner so as to allow the CD direction to coincide with the roll rotation direction of a preheating apparatus as shown in FIG. 2. Thus, the preheated nonwoven fabric layered body was obtained. The obtained nonwoven fabric layered body was immediately inserted in a manner so as to allow the CD direction to coincide with the roll rotation direction of a gear processing machine as shown in FIG. 1. Thus, the nonwoven fabric layered body that had been gear-drawn in the MD direction (machine direction of the nonwoven fabric layered body) was obtained. Preheating was controlled so as to adjust the roll surface temperature to 60° C., and gear rolls each mounted on the gear processing machine was set to have a diameter of 200 mm, a gear pitch of 2.5 mm, and a roll engagement depth of 5.5 mm. Ten evaluators evaluated texture of the nonwoven fabric layered body obtained by gear drawing described above by checking hand feeling based on the following criteria.

3: Ten out of 10 persons evaluated that there was no roughness.
2: Seven to nine out of 10 persons evaluated that there was no roughness.
1: Three to six out of 10 persons evaluated that there was no roughness.
0: Zero to two out of 10 persons evaluated that there was no roughness.

(7) Rate of Remaining Bosses [%]

A nonwoven fabric layered body that had been gear-drawn by the same method as in texture evaluation was evaluated in terms of the rate of remaining bosses via shape observation by SEM. It was determined that texture was more favorable with a higher rate of remaining bosses. The rate of remaining bosses was calculated by the following equation.

Rate of remaining bosses=Number of non-damaged bosses/Number of observed bosses×100

It was determined that embossed portions, for which hole formation or fiber elimination in embossed portions and fiber breakage in embossed portions and the boundary therebetween had not been observed, were designated as "non-damaged bosses" via SEM observation of embossed portions of the nonwoven fabric layered body that had been gear-drawn.

(8) Diaper Wearability

A test piece having a length of 250 mm in the machine direction (MD) and a length of 200 mm in the cross direction (CD) was collected from a nonwoven fabric layered body. The test piece was inserted in a manner so as to allow the CD direction to coincide with the roll rotation direction of a preheating apparatus as shown in FIG. 2. Thus, the preheated nonwoven fabric layered body was obtained. The obtained nonwoven fabric layered body was immediately inserted in a manner so as to allow the CD direction to coincide with the roll rotation direction of a gear processing machine as shown in FIG. 1. Thus, the nonwoven fabric layered body that had been gear-drawn in the MD direction (machine direction of the nonwoven fabric layered body)

was obtained. Preheating was controlled so as to adjust the roll surface temperature to 60° C., and gear rolls each mounted on the gear processing machine was set to have a diameter of 200 mm, a gear pitch of 2.5 mm, and a roll engagement depth of 3.5 mm. A nonwoven fabric was removed from a commercially available diaper, and the nonwoven fabric layered body obtained by gear drawing described above was bonded thereto. Ten evaluators wore the diaper and evaluated wearability based on the following criteria.

3: Ten out of 10 persons evaluated that there was no looseness.

2: Seven to nine out of 10 persons evaluated that there was no looseness.

1: Three to six out of 10 persons evaluated that there was no looseness.

0: Zero to two out of 10 persons evaluated that there was no looseness.

(9) Peel Strength [N] (Roll Blocking Resistance)

Roll blocking resistance of a nonwoven fabric layered body was evaluated by the method described below.

A 4-kg weight (10 cm×10 cm in square size) was placed on two overlapping sheets of nonwoven fabric layered bodies and stored in an oven at 90° C. for 2 hours. After storage for 2 hours, peel strength of the nonwoven fabric layered bodies taken from the oven was measured. As a result of this measurement, the peel strength was designated as an index of the ease of blocking due to storage environment temperature or pressure, in a case in which a nonwoven fabric layered body was stored in the roll form. In other words, smaller peel strength means more difficult blocking and higher blocking resistance. Peel strength was measured by the method described below.

Two test pieces having a length of 10.0 cm in the machine direction (MD) and a length of 5.0 cm in the cross direction (CD) were collected from the overlapping sheets of nonwoven fabric layered bodies, which had been taken from the oven. Next, a 15.0-cm piece was cut from packing tape, which was "Fabric tape No. 159 with a width of 50 mm manufactured by Teraoka Seisakusho Co., Ltd.", and bonded to the entire surface of the test piece in a manner so as to allow the machine direction (MD) of the test piece to coincide with the longitudinal direction of the packing tape. The packing tape was bonded to both sides of the test piece, thereby preparing a three-layer structure of packing tape/overlapping sheets of nonwoven fabric layered bodies/packing tape. Next, peel strength [N] of overlapping sheets of the nonwoven fabric layered bodies was measured by attaching the packing tapes bonded to the both sides of the three-layer structure to the upper and lower chucks of a low-rate extension type tensile tester and pulling at a chuck interval of 50 mm and a tensile speed of 100 mm/minute. Peel strength was calculated by rounding the mean of the values obtained for two sheets of test pieces off to two decimal places. In a case in which fixation was strong to an extent that caused a failure of adherend, peel strength of the overlapping sheets of the nonwoven fabric layered bodies was determined to be "adherend failure".

Example 1

<Synthesis of Low-Crystalline Polypropylene>

Continuous supply of n-heptane at 20 L/h, triisobutylaluminum at 15 mmol/h, and a catalyst component, which had been prepared in advance by bringing dimethylanilinium tetrakis(pentafluorophenyl)borate, (1,2'-dimethylsilylene) (2,1'-dimethylsilylene)-bis(3-trimethylsilyl methylindenyl) zirconiumdichloride, triisobutylaluminum, and propylene into contact with one another, at 6 μmol/h in terms of the zirconium content, to a stainless-steel reactor equipped with a stirrer having an inner volume of 0.2 m³ was conducted.

Propylene and hydrogen were continuously supplied so that the gas phase hydrogen concentration was maintained at 8 mol % and the total pressure inside of the reactor was maintained at 0.7 MPa·G at a polymerization temperature of 70° C.

SUMILIZER GP (manufactured by Sumitomo Chemical Co., Ltd.) was added to the obtained polymerization solution so as to result in a concentration of 1000 ppm, and the solvent was removed. Thus, a propylene polymer was obtained.

The weight average molecular weight (Mw) of the obtained propylene polymer was $1.2 \times 10^4$ with Mw/Mn=2. In addition, as a result of NMR measurement, [mmmm] was 46 mol %, [rrrr]/(1-[mmmm]) was 0.038, [rmrm] was 2.7 mol %, and $[mm] \times [rr]/[mr]^2$ was 1.5.

<Synthesis of Propylene.Ethylene.1-Butene Copolymer>

Dry hexane in a volume of 833 mL, 100 g of 1-butene, and triisobutylaluminum (1.0 mmol) were introduced at ordinary temperature into a polymerization apparatus having a volume of 2000 mL, which was sufficiently purged with nitrogen. Thereafter, the inner temperature of the polymerization apparatus was increased to 40° C., and the polymerization apparatus was pressurized by introducing propylene. Then, the pressure inside of the system was adjusted to 0.8 MPa by introducing ethylene.

Subsequently, a toluene solution containing 0.001 mmol of dimethylmethylene (3-tert-butyl-5-methylcyclopentadienyl)fluorenyl zirconiumdichloride and 0.3 mmol of methylaluminoxane (manufactured by Tosoh Finechem Corporation) in terms of the aluminum content was added to the polymerization apparatus. Thereafter, polymerization was allowed to take place for 20 minutes while maintaining the inner temperature at 40° C. and the pressure inside of the system at 0.8 MPa by introducing ethylene. Thereafter, 20 mL of methanol was added to terminate polymerization. After pressure release, a polymer precipitate was formed from the polymerization solution in 2 liters of methanol and dried at 130° C. for 12 hours under vacuum.

For the obtained polymer, the propylene content was 78 mol %, the ethylene content was 16 mol %, and the 1-butene content was 6 mol %. The melting point was 161° C., the crystallization degree was 6%, and the tensile elastic modulus was 23.5 MPa. A propylene.ethylene.1-butene (C2/C3/C4) copolymer obtained in the above manner is designated as PEB-1.

<Production of Nonwoven Fabric Layered Body>

A propylene homopolymer (hereinafter referred to as "polymer I") having an MFR (measured at a temperature of 230° C. and a load of 2.16 kg in accordance with ASTM D1238) of 8.5 g/10 minutes, a density of 0.91 g/cm³, and a melting point of 160° C. was melted using a 50-mmφ extruder. Separately, propylene homopolymer (hereinafter referred to as "polymer II") having an MFR (measured at a temperature of 230° C. and a load of 2.16 kg in accordance with ASTM D1238) of 60 g/10 minutes, a density of 0.91 g/cm³, a melting point of 160° C. was melted using a 75-mmφ extruder. Thereafter, a spunbond nonwoven fabric forming machine (length in a direction perpendicular to the machine direction on the collecting face: 800 mm) having a spinneret (die having 2887 holes) capable of forming a concentric core sheath composite fiber having a core made of "polymer I" and a sheath made of "polymer II" was used for conducting composite and melt spinning by the spunbond method at both resin and die temperatures of 250° C., a cooling air temperature of 20° C., and a drawing air wind speed of 3750 m/minute. Thus, an extensible spunbond nonwoven fabric comprising a concentric core-sheath-type composite fiber having a mass ratio of the core portion and the sheath portion of 10/90 was deposited as a first layer on the collecting face.

Subsequently, an elastic nonwoven fabric was deposited as a second layer on the face on which the extensible spunbond nonwoven fabric had been deposited. Specifically, a raw material, which had been prepared in advance by blending the low-crystalline polypropylene synthesized in the above step and PEB-1 at a mass ratio of 95:5, was melted using a monoaxial extruder having a screw diameter of 75 mmφ. Thereafter, a spunbond nonwoven fabric forming machine (length in a direction perpendicular to the machine direction on the collecting face: 800 mm) having a spinneret (die having 808 holes) was used for conducting melt spinning of the melted raw material by the spunbond method at both resin and die temperatures of 215° C., a cooling air temperature of 20° C., and a drawing air wind speed of 3750 m/minutes. Thus, the resulting fiber was deposited as a second layer.

Subsequently, as in the case of the first layer, a core-sheath-type composite fiber was deposited as a third layer on the second layer comprising the elastic nonwoven fabric by the same method as in the case of the first layer, thereby preparing a deposit having a three-layer structure. This deposit was processed by heating and pressurizing treatment using an embossing roll (at an embossed area rate of 18% and an embossing temperature of 70° C.), thereby preparing a nonwoven fabric layered body having a total weight per area of 30.0 g/m², a weight per area of 10.0 g/m² for the first and third layers, and a weight per area of 10.0 g/m² for the second layer (with a mass fraction of the elastic nonwoven fabric layer with respect to the total mass of 33.3%).

The nonwoven fabric layered body obtained as described above did not substantially adhere to the metal roll surface in the embossing step, indicating good formability. In addition, when the nonwoven fabric layered body was wound into a roll, it was easy to pull it out without roll blocking.

Table 1 shows the results of measurement of individual physical properties of the obtained nonwoven fabric layered body. The obtained nonwoven fabric layered body had favorable results in terms of the maximum load, degree of maximum load elongation, and residual strain.

Example 2

A nonwoven fabric layered body was produced in the same manner as in Example 1 except that the low-crystalline polypropylene and PEB-1 synthesized in Example 1 were blended at a mass ratio of 90:10 and the embossing temperature was changed to 75° C.

The nonwoven fabric layered body obtained as described above did not substantially adhere to the metal roll surface in the embossing step, indicating good formability. In addition, when the nonwoven fabric layered body was wound into a roll, it was easy to pull it out without roll blocking.

Table 1 shows the results of measurement of individual physical properties of the obtained nonwoven fabric layered body. The nonwoven fabric layered body had favorable results in terms of the maximum load, degree of maximum load elongation, and residual strain.

Example 3

A nonwoven fabric layered body was produced in the same manner as in Example 1 except that the low-crystalline polypropylene and PEB-1 synthesized in Example 1 were blended at a mass ratio of 80:20 and the embossing temperature was changed to 80° C.

The nonwoven fabric layered body obtained as described above did not substantially adhere to the metal roll surface in the embossing step, indicating good formability. In addition, when the nonwoven fabric layered body was wound into a roll, it was easy to pull it out without roll blocking.

Table 1 shows the results of measurement of individual physical properties of the obtained nonwoven fabric layered body. The nonwoven fabric layered body had favorable results in terms of the maximum load, degree of maximum load elongation, residual strain, rate of remaining bosses, texture, and wearability. In addition, the test piece could be peeled without being broken (adherend failure) upon evaluation of roll blocking resistance, which was favorable.

Example 4

A nonwoven fabric layered body was produced in the same manner as in Example 1 except that the low-crystalline polypropylene and PEB-1 synthesized in Example 1 were blended at a mass ratio of 60:40 and the embossing temperature was changed to 95° C.

The nonwoven fabric layered body obtained as described above did not substantially adhere to the metal roll surface in the embossing step, indicating good formability. In addition, when the nonwoven fabric layered body was wound into a roll, it was easy to pull it out without roll blocking.

Table 1 shows the results of measurement of individual physical properties of the obtained nonwoven fabric layered body. The nonwoven fabric layered body had favorable results in terms of the maximum load, degree of maximum load elongation, and residual strain. In addition, the test piece could be peeled without being broken (adherend failure) upon evaluation of roll blocking resistance, which was favorable.

Example 5

A nonwoven fabric layered body was produced in the same manner as in Example 1 except that the low-crystalline polypropylene and PEB-1 synthesized in Example 1 were blended at a mass ratio of 50:50 and the embossing temperature was changed to 105° C.

The nonwoven fabric layered body obtained as described above did not substantially adhere to the metal roll surface in the embossing step, indicating good formability. In addition, when the nonwoven fabric layered body was wound into a roll, it was easy to pull it out without roll blocking.

Table 1 shows the results of measurement of individual physical properties of the obtained nonwoven fabric layered body. The nonwoven fabric layered body had favorable results in terms of the maximum load, degree of maximum load elongation, and residual strain.

Example 6

A nonwoven fabric layered body was produced in the same manner as in Example 1 except that PEB-1 synthesized in Example 1 was replaced by Vistamaxx 2120 (manufactured by ExxonMobil, ethylene.propylene (C2/C3) copolymer having a melting point of 162° C., a crystallization degree of 10%, and a tensile elastic modulus of 30.9 MPa), the low-crystalline polypropylene synthesized in Example 1 and Vistamaxx 2120 were blended at a mass ratio of 60:40, and the embossing temperature was changed to 105° C.

The nonwoven fabric layered body obtained as described above did not substantially adhere to the metal roll surface in the embossing step, indicating good formability. In addition, when the nonwoven fabric layered body was wound into a roll, it was easy to pull it out without roll blocking.

Table 1 shows the results of measurement of individual physical properties of the obtained nonwoven fabric layered body. The nonwoven fabric layered body had favorable results in terms of the maximum load, degree of maximum load elongation, and residual strain.

Comparative Example 1

A nonwoven fabric layered body was produced in the same manner as in Example 1 except that the second layer was changed to a layer consisting of the low-crystalline polypropylene synthesized in Example 1.

The nonwoven fabric layered body obtained as described above did not substantially adhere to the metal roll surface in the embossing step, indicating good formability. In addition, when the nonwoven fabric layered body was wound into a roll, it was easy to pull it out without roll blocking.

Table 1 shows the results of measurement of individual physical properties of the obtained nonwoven fabric layered body. The obtained nonwoven fabric layered body had favorable results in terms of maximum load and degree of maximum load elongation; however, it had a large residual strain, a low rate of remaining bosses, and low evaluation in terms of texture. In addition, the test piece was broken during the test of roll blocking resistance (adherend failure: 11 N or more), indicating poor results in terms of roll blocking resistance.

Comparative Example 2

A nonwoven fabric layered body was produced in the same manner as in Example 1 except that the low-crystalline polypropylene and PEB-1 synthesized in Example 1 were blended at a mass ratio of 40:60 and the embossing temperature was changed to 120° C.

The nonwoven fabric layered body obtained as described above did not substantially adhere to the metal roll surface in the embossing step, indicating good formability. In addition, when the nonwoven fabric layered body was wound into a roll, it was easy to pull it out without roll blocking.

Table 1 shows the results of measurement of individual physical properties of the obtained nonwoven fabric layered body. The obtained nonwoven fabric layered body had favorable results in terms of maximum load and residual strain; however, it had a low degree of maximum load elongation.

Comparative Example 3

<Production of Ethylene.1-Butene Copolymer>
(Preparation of Catalyst Solution)

Triphenylcarbenium tetrakis(pentafluorophenyl)borate in an amount of 18.4 mg was collected, 5 mL of toluene was added to dissolve it, thereby preparing a toluene solution at a concentration of 0.004 millimole/mL. In addition, 1.8 mg of [dimethyl(t-butylamide)(tetramethyl-$\eta^5$-cyclopentadienyl)silane]titanium dichloride was collected, and 5 mL of toluene was added to dissolve it, thereby preparing a toluene solution at a concentration of 0.001 millimole/mL.

At the start of polymerization, 0.38 mL of the toluene solution of triphenylcarbenium tetrakis(pentafluorophenyl) borate and 0.38 mL of the toluene solution of [dimethyl(t-butylamide)(tetramethyl-$\eta^5$-cyclopentadienyl)silane]titanium dichloride were collected, and 4.24 mL of a toluene diluent was further added thereto. Thus, 5 mL of a toluene solution, in which the concentration of triphenylcarbenium tetrakis(pentafluorophenyl)borate was 0.002 millimole/liter in terms of the B content and the concentration of [dimethyl (t-butylamide)(tetramethyl-$\eta^5$-cyclopentadienyl)silane]titanium dichloride was 0.0005 millimole/liter in terms of the Ti content, was prepared and used as a catalyst solution.

(Polymerization)

Heptane in a volume of 750 mL was introduced into an SUS autoclave equipped with a stirrer blade having a volume of 1.5 liter, which had been sufficiently purged with nitrogen, at 23° C. 1-Butene in an amount of 6 g and 150 mL of hydrogen were introduced into the autoclave while rotating the stirrer blade during ice cooling. Next, this autoclave was heated to 100° C., and further pressurized with ethylene so that the total pressure reached to 6 kg/cm$^2$. When the inner pressure of the autoclave reached 6 kg/cm$^2$, 1.0 mL of a hexane solution containing triisobutylaluminum (TIBA) at a concentration of 1.0 millimole/mL was injected with nitrogen. Then, 5 mL of a toluene solution of the catalyst described above was injected into the autoclave with nitrogen, thereby initiating polymerization. Thereafter, the temperature was controlled for 5 minutes so that the inner temperature of the autoclave reached 100° C., and ethylene was directly supplied so that the pressure reached 6 kg/cm$^2$. Five minutes after the initiation of polymerization, 5 mL of methanol was introduced into the autoclave via a pump to terminate polymerization. The pressure of the autoclave was released to reach the atmospheric pressure. Three liters of methanol was poured into the reaction solution during stirring. The obtained polymer containing the solvent was dried at 130° C. for 13 hours at 600 Torr (80000 Pa). For the obtained polymer, the ethylene content was 88 mol %, the 1-butene content was 12 mol %, the melting point was 70° C., the crystallization degree was 24%, and the tensile elastic modulus was 23.5 MPa. An ethylene.1-butene (C2/C4) copolymer obtained in the above manner is designated as EB-2.

<Production of Nonwoven Fabric Layered Body>

In order to form a second layer, the low-crystalline polypropylene synthesized in Example 1 and EB-2 synthesized above were blended at a mass ratio of 60:40. However, it resulted in very poor spinnability and a nonwoven fabric layered body could not be obtained.

Comparative Example 4

<Production of Propylene.1-Butene Copolymer>

Hexane in a volume of 900 mL and 90 g of 1-butene were introduced into a 2-liter autoclave, which had been sufficiently purged with nitrogen, 1 millimole of triisobutylaluminum was added thereto, and the temperature was increased to 70° C. Thereafter, propylene was supplied to adjust the total pressure to 7 kg/cm$^2$ G, and 0.30 millimoles of methylaluminoxane and 0.001 millimole of rac-dimethylsilylene-bis{1-(2-methyl-4-phenylindenyl)}zirconiumdichloride produced in the same manner as in the example of production of PEB-1 described above in terms of the content of Zr atoms were added. Polymerization was conducted for 30 minutes while continuously supplying propylene to maintain the total pressure at 7 kg/cm$^2$ G. After polymerization, degassing was conducted. A polymer was recovered in a large amount of methanol and depressurized and dried at 110° C. for 12 hours. For the obtained polymer, the propylene content was 74 mol %, the 1-butene content was 26 mol %, the melting point was 77° C., the crystallization degree was 19%, and the tensile elastic modulus was 217.3 MPa. The propylene.1-butene (C3/C4) copolymer obtained in the above manner is designated as PB-3.

<Production of Nonwoven Fabric Layered Body>

A nonwoven fabric layered body was produced in the same manner as in Example 1 except that the low-crystalline polypropylene synthesized in Example 1 and PB-3 synthesized above were blended at a mass ratio of 60:40 for the second layer and the embossing temperature was changed to 105° C.

The nonwoven fabric layered body obtained as described above did not substantially adhere to the metal roll surface in the embossing step, indicating good formability. In addition, when the nonwoven fabric layered body was wound into a roll, it was easy to pull it out without roll blocking.

Table 1 shows the results of measurement of individual physical properties of the obtained nonwoven fabric layered body. The obtained nonwoven fabric layered body had a small degree of maximum load elongation and a large residual strain.

Comparative Example 5

A nonwoven fabric layered body was produced in the same manner as in Example 1 except that the low-crystalline polypropylene synthesized in Example 1 and Affinity PL 1850 (manufactured by Dow Chemical Company: an ethylene.1-octene (C2/C8) copolymer having a melting point of 100° C., a crystallization degree of 35%, and a tensile elastic modulus of 75.4 MPa) were blended at a mass ratio of 95:5 for the second layer and the embossing temperature was changed to 80° C.

The nonwoven fabric layered body obtained as described above did not substantially adhere to the metal roll surface in the embossing step, indicating good formability. In addition, when the nonwoven fabric layered body was wound into a roll, it was easy to pull it out without roll blocking.

Table 1 shows the results of measurement of individual physical properties of the obtained nonwoven fabric layered body. The obtained nonwoven fabric layered body had a large residual strain.

Comparative Example 6

In order to form a second layer, the low-crystalline polypropylene synthesized in Example 1 and Affinity PL 1850 (manufactured by Dow Chemical Company: an ethylene.1-octene (C2/C8) copolymer having a melting point of 100° C., a crystallization degree of 35%, and a tensile elastic modulus of 75.4 MPa) were blended at a mass ratio of 60:40. However, it resulted in very poor spinnability, and therefore, a nonwoven fabric layered body could not be obtained.

Comparative Example 7

In order to form a second layer, the low-crystalline polypropylene synthesized in Example 1 and Engage 8407 (manufactured by Dow Chemical Company: an ethylene.1-octene (C2/C8) copolymer having a melting point of 63° C., a crystallization degree of 26%, and a tensile elastic modulus of 8.2 MPa) were blended at a mass ratio of 60:40. However, it resulted in very poor spinnability, and therefore, a nonwoven fabric layered body could not be obtained.

Comparative Example 8

A nonwoven fabric layered body was produced in the same manner as in Example 1 except that the low-crystalline polypropylene synthesized in Example 1 and Prime Polypro S119 (manufactured by Prime Polymer Co., Ltd.: a polypropylene (C3) homopolymer having a melting point of 160° C., a crystallization degree of 50%, and a tensile elastic modulus of 1570 MPa) were blended at a mass ratio of 80:20 for the second layer and the embossing temperature was changed to 85° C.

The nonwoven fabric layered body obtained as described above did not substantially adhere to the metal roll surface in the embossing step, indicating good formability. In addition, when the nonwoven fabric layered body was wound into a roll, it was easy to pull it out without roll blocking.

Table 1 shows the results of measurement of individual physical properties of the obtained nonwoven fabric layered body. The obtained nonwoven fabric layered body had a small degree of maximum load elongation, a large residual strain, and poor texture.

TABLE 1

| | | | Example 1 | Example 2 | Example 3 | Example 4 | Example 5 | Example 6 |
|---|---|---|---|---|---|---|---|---|
| Elastic nonwoven fabric (a) | α-olefin copolymer A | Type | PEB-1 | PEB-1 | PEB-1 | PEB-1 | PEB-1 | Vistamaxx 2120 |
| | | Structure | C2/C3/C4 | C2/C3/C4 | C2/C3/C4 | C2/C3/C4 | C2/C3/C4 | C2/C3 |
| | | Melting point [° C.] | 161 | 161 | 161 | 161 | 161 | 162 |
| | | Crystallization degree [%] | 6 | 6 | 6 | 6 | 6 | 10 |
| | | Elastic modulus [MPa] | 23.5 | 23.5 | 23.5 | 23.5 | 23.5 | 30.9 |
| | | Blending ratio [%] | 5 | 10 | 20 | 40 | 50 | 40 |
| | Low-crystalline PP | Blending ratio [%] | 95 | 90 | 80 | 60 | 50 | 60 |
| | Weight per area | [g/m$^2$] | 10 | 10 | 10 | 10 | 10 | 10 |
| | Spinnability | [—] | A | A | A | A | A | A |
| Extensible SB nonwoven fabric (b) | Structure | — | Core-sheath | Core-sheath | Core-sheath | Core-sheath | Core-sheath | Core-sheath |
| | Resin | — | PP/PP | PP/PP | PP/PP | PP/PP | PP/PP | PP/PP |
| | Weight per area | [g/m$^2$] | 10 | 10 | 10 | 10 | 10 | 10 |
| | Degree of maximum load elongation | [%] | 155 | 155 | 155 | 155 | 155 | 155 |
| Nonwoven fabric layered body (b/a/b) | Weight per area | [g/m$^2$] | 30 | 30 | 30 | 30 | 30 | 30 |
| | Maximum load | [N/50 mm] | 34.7 | 34.8 | 37.9 | 37.7 | 39.0 | 36.8 |
| | Degree of maximum load elongation | [%] | 239 | 231 | 240 | 242 | 213 | 215 |
| | Residual strain | [%] | 24.6 | 24.3 | 23.6 | 22.6 | 21.4 | 22.9 |
| | Formability | [—] | A | A | A | A | A | A |
| | Texture (after drawing) | [—] | — | — | 3 | — | — | 3 |
| | Rate of remaining bosses | [%] | — | — | 75 | — | — | — |

TABLE 1-continued

| | | | | | | | | | | | |
|---|---|---|---|---|---|---|---|---|---|---|---|
| | Wearability | [—] | — | — | 3 | — | — | | | | |
| | Peel strength | [N] | — | — | 0.98 | 0.50 | — | | | | |

| | | | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|---|---|---|
| Elastic nonwoven fabric (a) | α-olefin copolymer A | Type | N/A | PEB-1 | EB-2 | PB-3 | Affinity PL 1850 | Affinity PL 1850 | Engage 8407 | S119 |
| | | Structure | — | C2/C3/C4 | C2/C4 | C3/C4 | C2/C8 | C2/C8 | C2/C8 | C3 |
| | | Melting point [° C.] | — | 161 | 70 | 77 | 100 | 100 | 63 | 160 |
| | | Crystallization degree [%] | — | 6 | 24 | 19 | 35 | 35 | 26 | 50 |
| | | Elastic modulus [MPa] | — | 23.5 | 23.5 | 217.3 | 75.4 | 75.4 | 8.2 | 1570 |
| | | Blending ratio [%] | 0 | 60 | 40 | 40 | 5 | 40 | 40 | 20 |
| | Low-crystalline PP | Blending ratio [%] | 100 | 40 | 60 | 60 | 95 | 60 | 60 | 80 |
| | Weight per area | [g/m$^2$] | 10 | 10 | 10 | 10 | 10 | 10 | 10 | 10 |
| | Spinnability | [—] | A | A | C | A | A | C | C | A |
| Extensible SB nonwoven fabric (b) | Structure | — | Core-sheath | Core-sheath | Core-sheath | Core-sheath | Core-sheath | Core-sheath | Coresheath | Coresheath |
| | Resin | — | PP/PP | PP/PP | PP/PP | PP/PP | PP/PP | PP/PP | PP/PP | PP/PP |
| | Weight per area | [g/m$^2$] | 10 | 10 | 10 | 10 | 10 | 10 | 10 | 10 |
| | Degree of maximum load elongation | [%] | 155 | 155 | 155 | 155 | 155 | 155 | 155 | 155 |
| Nonwoven fabric layered body (b/a/b) | Weight per area | [g/m$^2$] | 30 | 30 | — | 30 | 30 | 30 | 30 | 30 |
| | Maximum load | [N/50 mm] | 35.5 | 38.5 | — | 37.4 | 41.3 | — | — | 32.8 |
| | Degree of maximum load elongation | [%] | 224 | 200 | — | 181 | 249 | — | — | 133 |
| | Residual strain | [%] | 26.4 | 20.1 | — | 34.4 | 37.5 | — | — | 40.9 |
| | Formability | [—] | A | A | — | A | A | — | — | A |
| | Texture (after drawing) | [—] | 1 | — | — | — | — | — | — | 1 |
| | Rate of remaining bosses | [%] | 57 | — | — | — | — | — | — | — |
| | Wearability | [—] | 1 | — | — | — | — | — | — | — |
| | Peel strength | [N] | Adherend failure | — | — | — | — | — | — | — |

The disclosure of Japanese Patent Application No. 2015-046377 is incorporated herein by reference in its entirety. All publications, patent applications, and technical standards mentioned in this specification are herein incorporated by reference to the same extent as if each individual publication, patent application, or technical standard was specifically and individually indicated to be incorporated by reference.

The invention claimed is:

1. A nonwoven fabric layered body, comprising:
an elastic nonwoven fabric; and
an extensible spunbond nonwoven fabric that is disposed on at least one surface side of the elastic nonwoven fabric and that has a degree of maximum load elongation of 50% or more in at least one direction,
the nonwoven fabric layered body satisfying the following (1) and (2):
(1) the elastic nonwoven fabric comprises a resin composition containing a low-crystalline polypropylene satisfying the following (a) to (f), and an α-olefin copolymer A containing constitutional units derived from ethylene, propylene and butene, and having a melting point of 150° C. or more and a crystallization degree of 8% or less, and
(2) the resin composition contains from 5 parts by mass to 50 parts by mass of the α-olefin copolymer A with respect to 100 parts by mass of the resin composition:

(a) [mmmm]=20 to 60 mol %
(b) [rrrr]/(1−[mmmm])≤0.1
(c) [rmrm]>2.5 mol %
(d) [mm]×[rr]/[mr]$^2$≤2.0
(e) weight average molecular weight (Mw)=10,000 to 200,000
(f) molecular weight distribution (Mw/Mn)<4,
wherein, in (a) to (d), [mmmm] represents a meso pentad fraction, [rrrr] represents a racemic pentad fraction, [rmrm] represents a racemic meso racemic meso pentad fraction, and [mm], [rr] and [mr] each represent a triad fraction.

2. The nonwoven fabric layered body according to claim 1, wherein the resin composition contains from 95 parts by mass to 50 parts by mass of the low-crystalline polypropylene with respect to 100 parts by mass of the resin composition.

3. The nonwoven fabric layered body according to claim 1, wherein the α-olefin copolymer A has a tensile elastic modulus of 100 MPa or less.

4. The nonwoven fabric layered body according to claim 1, wherein the extensible spunbond nonwoven fabric is disposed on both surface sides of the elastic nonwoven fabric.

5. The nonwoven fabric layered body according to claim 1, wherein the elastic nonwoven fabric is a nonwoven fabric obtained by a spunbond method.

6. The nonwoven fabric layered body according to claim 1, wherein the extensible spunbond nonwoven fabric is an extensible spunbond nonwoven fabric comprising a concentric core-sheath-type composite fiber comprising, as a core portion, a low-MFR propylene-based polymer having an MFR in a range of from 1 g/10 minutes to 200 g/10 minutes and, as a sheath portion, a high-MFR propylene-based polymer having an MFR in a range of from 16 g/10 minutes to 215 g/10 minutes, and wherein a difference in MFR between the low-MFR propylene-based polymer and the high-MFR propylene-based polymer is 15 g/10 minutes or more, wherein MFR is referred to as melt flow rate.

7. The nonwoven fabric layered body according to claim 1, wherein the extensible spunbond nonwoven fabric comprises an olefin-based polymer composition containing from 80% by mass to 99% by mass of a crystalline propylene-based polymer and from 1% by mass to 20% by mass of a high-density polyethylene.

8. The nonwoven fabric layered body according to claim 1, wherein a weight-per-area ratio of the elastic nonwoven fabric and the extensible spunbond nonwoven fabric (elastic nonwoven fabric: extensible spunbond nonwoven fabric) is in a range of from 10:90 to 90:10.

9. A stretchable nonwoven fabric layered body, obtained by drawing the nonwoven fabric layered body according to claim 1.

10. A fiber product, comprising the nonwoven fabric layered body according to claim 1.

11. An absorbent article, comprising the nonwoven fabric layered body according to claim 1.

12. A sanitary mask, comprising the nonwoven fabric layered body according to claim 1.

13. A fiber product, comprising the stretchable nonwoven fabric layered body according to claim 9.

14. An absorbent article, comprising the stretchable nonwoven fabric layered body according to claim 9.

15. A sanitary mask, comprising the stretchable nonwoven fabric layered body according to claim 9.

* * * * *